United States Patent
Lindquist

(10) Patent No.: US 8,790,286 B2
(45) Date of Patent: *Jul. 29, 2014

(54) INJECTION DISTRACTION DEVICE

(75) Inventor: Sherrill F Lindquist, Niveville, FL (US)

(73) Assignee: Raintree Essix, LLC, Metairie, LA (US)

( * ) Notice: Subject to any disclaimer, the term of this patent is extended or adjusted under 35 U.S.C. 154(b) by 757 days.

This patent is subject to a terminal disclaimer.

(21) Appl. No.: 12/730,162

(22) Filed: Mar. 23, 2010

(65) Prior Publication Data

US 2010/0178632 A1    Jul. 15, 2010

Related U.S. Application Data

(62) Division of application No. 11/043,674, filed on Jan. 26, 2005, now Pat. No. 7,686,773.

(51) Int. Cl.
*A61H 1/00* (2006.01)

(52) U.S. Cl.
USPC .......................................... 601/73; 433/122

(58) Field of Classification Search
USPC ............. 601/46, 67, 69, 70, 72, 73; 433/103, 433/114, 118, 122, 126, 131
See application file for complete search history.

(56) References Cited

U.S. PATENT DOCUMENTS

| | | | | |
|---|---|---|---|---|
| 2,140,307 A | * | 12/1938 | Belaschk et al. | 15/28 |
| 2,183,690 A | * | 12/1939 | Ostrom | 433/122 |
| 2,645,219 A | * | 7/1953 | Bertholin | 601/70 |
| 3,620,209 A | | 11/1971 | Kravitz | |
| 3,623,481 A | * | 11/1971 | Curran | 601/74 |
| 4,279,598 A | * | 7/1981 | Scheicher | 433/173 |
| 4,432,729 A | * | 2/1984 | Fattaleh | 433/118 |
| 4,608,019 A | | 8/1986 | Kumabe et al. | |
| 5,145,369 A | * | 9/1992 | Lustig et al. | 433/118 |
| 5,437,606 A | * | 8/1995 | Tsukamoto | 601/2 |
| 5,639,238 A | | 6/1997 | Fishburne, Jr. | |
| 5,647,851 A | * | 7/1997 | Pokras | 604/131 |
| 5,873,844 A | * | 2/1999 | Campero et al. | 601/2 |
| 6,183,427 B1 | * | 2/2001 | Ishii | 601/46 |
| 6,231,531 B1 | | 5/2001 | Lum et al. | |
| 7,686,773 B2 | * | 3/2010 | Lindquist | 601/2 |
| 2003/0165791 A1 | * | 9/2003 | Carmichael et al. | 433/72 |
| 2006/0135892 A1 | * | 6/2006 | Nan | 601/72 |

* cited by examiner

*Primary Examiner* — Justine Yu
*Assistant Examiner* — Kathrynn Reilly
(74) *Attorney, Agent, or Firm* — Joseph T Regard, Ltd plc

(57) ABSTRACT

A system for mitigating pain in a patient associated with needle penetration in the administration of medication, and in particular to a vibratory device configured to be utilized with a variety of existing hand-held intra-oral dental drills or like devices. The preferred embodiment of the present invention teaches a disposable or non-disposable vibratory tip formed to engage an off-the-shelf intra-oral dental drill, the vibratory tip utilizing an off-axis weight associated with a shaft drive engaging the dental drill, to provide a vibratory sensation to an application tip, the application tip configured to engage an area of a patient's mouth targeted for the subsequent needled administration of local anesthetic, or other medication. In use, the application tip is applied to the patient, the dental drill is engaged to rotate the shaft drive of the vibratory tip, vibrating same for period of time, so as to decrease the sensation of pain associated with the subsequent needle penetration.

3 Claims, 3 Drawing Sheets

INJECTION DISTRACTION DEVICE

PRIORITY CLAIM

The Present application is a divisional of U.S. Utility patent application Ser. No. 11/043,674 filed Jan. 26, 2005, now U.S. Pat. No. 7,686,733, listing as inventor Sherrill F. Lindquist.

TECHNICAL FIELD OF THE INVENTION

The present invention relates to systems for mitigating pain in a patient associated with an injection associated with the administration of medication, and in particular to a vibratory device configured to be connected to and utilized with a variety of existing hand-held intra-oral dental drills or like devices for numbing the target area prior to injection.

The preferred embodiment of the present invention teaches a disposable or non-disposable vibratory tip piece formed to engage an off-the-shelf dental hand piece, the vibratory tip utilizing an off-axis weight associated with a shaft drive for engaging the dental hand piece, the hand piece rotating the off-axis weight to provide a vibratory sensation to an application tip, the application tip configured to engage an area of a patient's mouth targeted for the subsequent needled administration of local anesthetic, or other medication.

In use, the application tip is applied to the patient, the dental drill is engaged to rotate the shaft drive of the vibratory tip, vibrating the application tip for a period of time, so as to numb the target area to decrease the sensation of pain associated with the subsequent needle penetration.

BACKGROUND OF THE INVENTION

Present conventional dental practice in the United States often involves the application of a viscous solution containing a topical anesthetic such as Benzocaine or the like to intra-oral soft tissues, to numb the target area prior to the needled insertion of a local anesthetic.

The dentist or other clinician applies the topical anesthetic with a cotton swab for 1-2 minutes to the soft tissue area where the dental injection will be inserted. The topical anesthetic deadens the perception of pain in the area where it was introduced.

Unfortunately, the anesthetic also may be spread by the patients tongue, resulting in an unpleasant taste and loss of sensation/control of the tongue and inadvertent numbing of other areas of the mouth; further, the anesthetic may be swallowed. In addition, the topical anesthetic takes time to work, and may not always be effective in sufficiently deadening the pain.

There therefore exists a need in the dental area for a means for deadening the sensation of a needle being introduced into the intra-oral tissues of a patient which does not require medication, which may be applied quickly and effectively, and in a safe, sterile and inexpensive manner.

GENERAL SUMMARY DISCUSSION OF THE INVENTION

Unlike the prior art, the present invention provides a system for numbing a target area on a patient particularly suitable for intra-oral use which requires no anesthetic, in a device which is inexpensive to procure and use, and is safe, sanitary, and effective in operation.

The present invention relates to the mitigation or elimination of intra-oral pain felt by a dental patient when receiving an intra-oral dental injection from a dentist or other licensed clinician, in order to anesthetize a particular intra-oral anatomical structure.

This mitigation or elimination of intra-oral pain is accomplished by the dentist or other licensed clinician by attaching a disposable or non-disposable piece of dental equipment (the vibrating tip) to an existing slow speed or variable speed dental hand piece and motor.

The application tip of the device of the present invention produces a vibration that, when held against the intra-oral soft tissue, produces a numbing sensation which, in turn, mitigates or eliminates the pain associated with a dental injection.

The Melzack and Wall gate control theory of pain (1965) offers a possible explanation as to how the mitigation or elimination of pain is caused by vibrating the tissue. Stimulation of larger diameter nerves (A fibers), which transmit the sensations of touch, pressure, and temperature are believed to block the transmission of smaller diameter nerves (A-delta and C-fibers), which carry sensations of pain.

This blockage, or closed gate, prevents the pain sensation from reaching the brain, where the sensation is perceived as pain.

In the present invention, the vibrating tip possibly functions as a deadening means by heavily stimulating the larger diameter A fibers, and consequently temporarily affecting the conduction of the smaller diameter A-delta and C-fibers.

An exemplary method of use of the present invention, utilizing the preferred device which will be discussed in greater detail infra, involves the following steps:

1) attaching the disposable or non-disposable vibrating tip device of the present invention to a slow or variable speed dental hand piece;

2) positioning the hand piece so that the attached vibrating tip is held against the intra-oral soft tissue (the target area) where the dental injection will be made;

3) initiating the rotation of the hand piece so as to rotate the drive shaft of the vibrating tip, driving the vibration means (for example, and off-balance weight), providing a vibrating tip;

4) holding the vibrating tip for a desired period of time to target area; and 5) removing the vibrating tip from the intra-oral soft tissue comprising the target area, and proceeding with the dental injection.

The present procedure, when utilized as a replacement for the prior art method of utilizing local topical anesthetic, has been found to provide equally satisfactory or improved results, realizes the reduction of required dentist time, and provides a procedure that tends to make the administration of dental injections a more positive experience.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein.

DETAILED DISCUSSION OF THE INVENTION

Figures 1, 2:
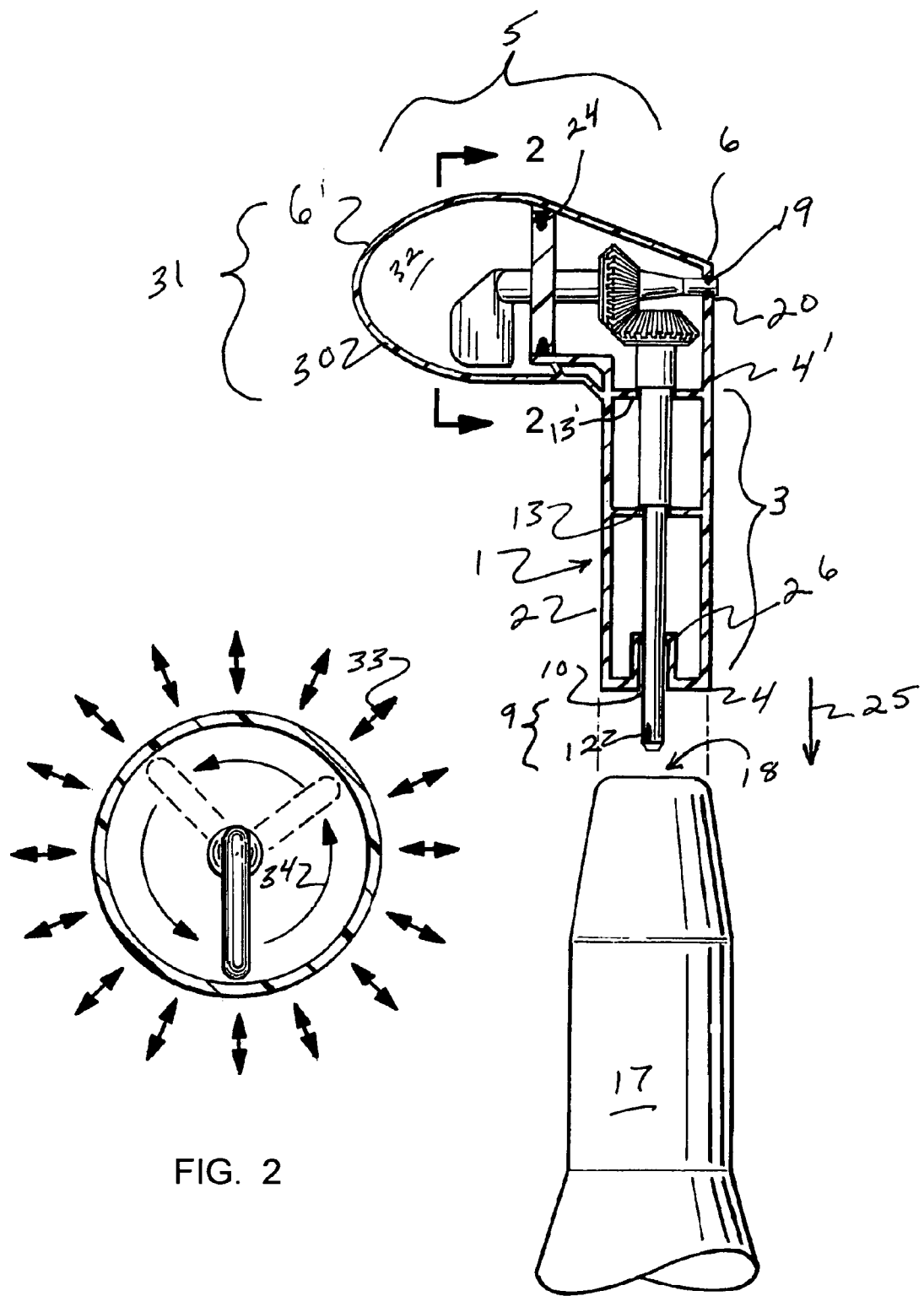
FIG. 1 is a side, partially cut-away view of the preferred exemplary embodiment of the present invention positioned for engagement to an exemplary off-the-shelf drive/hand piece.
FIG. 2 is a top, cut-away view of the off-center weight of the invention of FIG. 1 rotating via the driveshaft, causing vibration of the tip.
Figures 3, 4, 5:
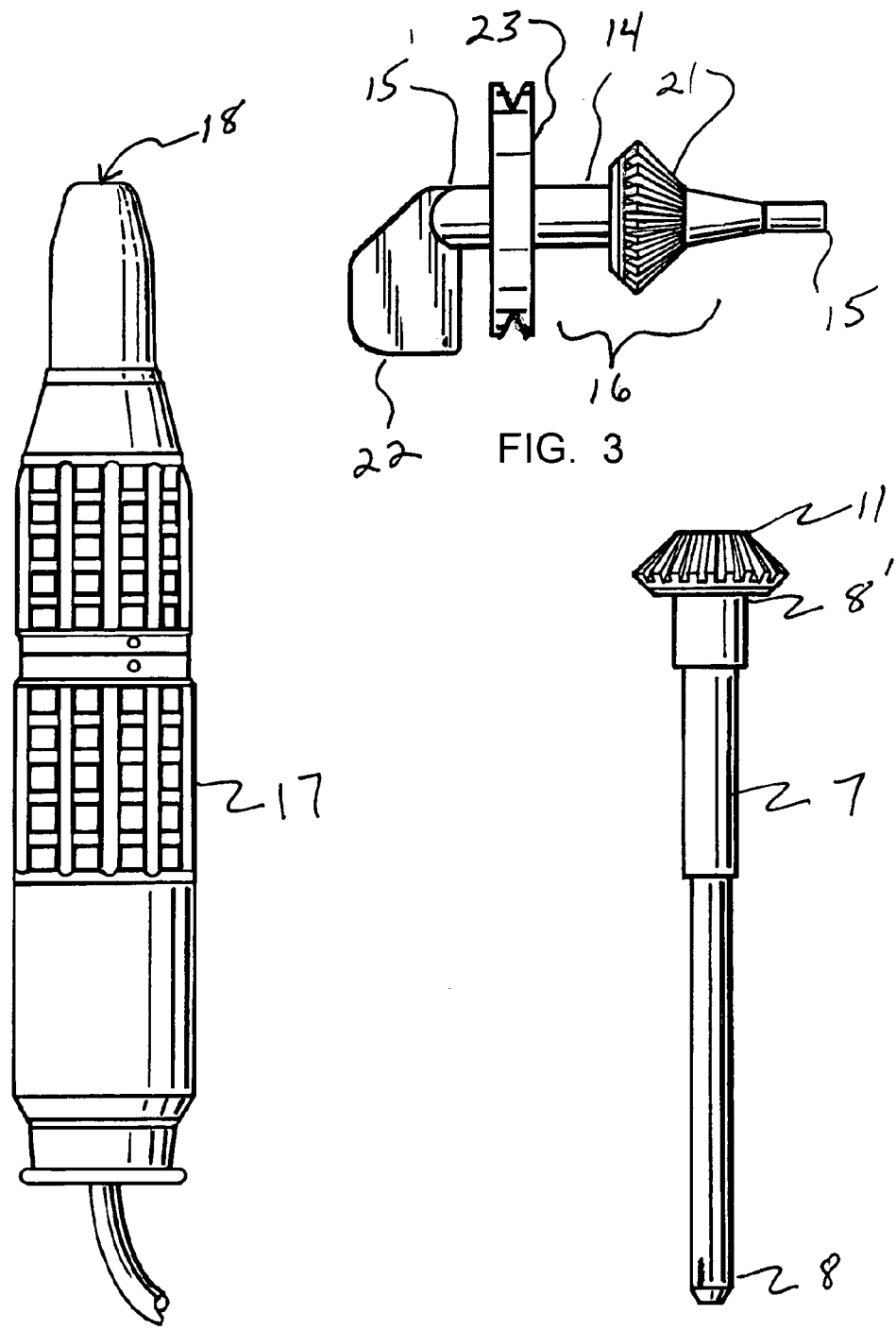
FIG. 3 is a side view of the lateral drive shaft of FIG. 1, having an off-center weight applied thereto.
FIG. 4 is a side view of the longitudinal drive shaft of the invention of FIG. 1.
FIG. 5 is a side view of an exemplary hand-held rotary drive unit.

Referring to FIGS. 1-5, the preferred embodiment of the present invention comprises a device 1 in the form of a vibrating application tip configured to engage a low speed or variable low speed dental hand piece in similar manner as existing dental prophylaxis cup angle (also referred to as a "prophy"). An example of a compatible hand piece used in the present system comprises, for example, the Midwest brand straight attachment 17, which fits upon a low speed motor, to provide a low speed dental hand piece.

It is iterated that there are several other manufacturers that provide low-speed dental hand pieces which would be compatible with the device 1 of the present invention, and other exemplary brands and models are listed infra, although said listing is not intended to be comprehensive or limiting.

The device 1 comprises an outer body casing 2 having a cavity there through, the casing comprising a longitudinal portion 3 having first 4 and second 4' ends, and a lateral portion 5 having first 6 and second ends 6', the lateral portion engaging the longitudinal portion at ends 4', 6', respectively.

Situated within the longitudinal portion 3 of the casing is a first drive shaft 7 having first 8 and second 8' ends, the first end 8 of the shaft 7 emanating 10 from the first end 4 of the longitudinal portion of the body to provide an exposed shank 9, the shank having a notch 12 for engaging 25 a chuck 18 situated at the end of the hand piece 17.

The second end 8' of the first drive shaft 7 has mounted thereon a 90 degree shaft gear 11. The first drive shaft 7 is rotatably supported within the longitudinal portion 3 of the casing via first 13 and second 13' support points.

Situated within the lateral portion 5 of the outer body casing is a second, laterally situated drive shaft 14 having first 15 and second 15' ends, and a medial portion 16 there between.

As shown, the first end 15 of the second shaft 14 engages the outer body casing at aperture 20, a gear nub 19 formed therein to rotatingly engage the end of the shaft. The first end of the second drive shaft is situated in the vicinity of the second end 8' of the first drive shaft 7, the second drive shaft having mounted thereon a 90 degree shaft gear 21 engaging the 90 degree shaft gear 11 mounted to the first drive shaft 7.

An off-center weight 22 is provided at the second end 15' of the second, lateral drive shaft 14, while a collar 23 is situated along shaft 14 between the off-center weight 22 and shaft gear 21, the collar 23 engaging a nub 24 where the periphery of the collar 23 rotatingly engages 25 the casing to rotatingly support the second drive shaft 14 in operation.

A shell/cover 30 is formed about the off-center weight 22 to provide a cavity 32 sufficient in size to allow the unimpeded rotation of the off-center weight therein, the outer surface of the shell/cover portion forming an application surface 31, the above design thereby providing a contra-angle vibrating tip which allows the dentist to have greater access to various locations in the oral cavity.

In use, the exposed shank 9 is placed into the chuck 18 of the hand piece 17, engaging same. A mechanical coupling, such as a notch 26 or alternatively a twist lock, as is commonly used in plastic fabrications, can also be provided to engage the first end 4 of the longitudinal portion 3 of the device to an engaging member formed at the tip of the hand piece.

The hand piece is then engaged, the chuck rotating the first drive shaft 8, which engages and rotates the second, lateral drive shaft 14, rotating 34 the off-center weight 22, causing a rapid circular motion resulting in a vibration 33, which vibration is transferred via the casing 2 to the application surface 31.

In treating a patient, the a motor drives the hand piece, which in turn drives the present device 1, rotating the off-center weight at a revolutions per minute (RPM) range of, for example, 1 to 40,000 RPMs, with a preferred RPM range of 500 to 6,000.

Figure 6:
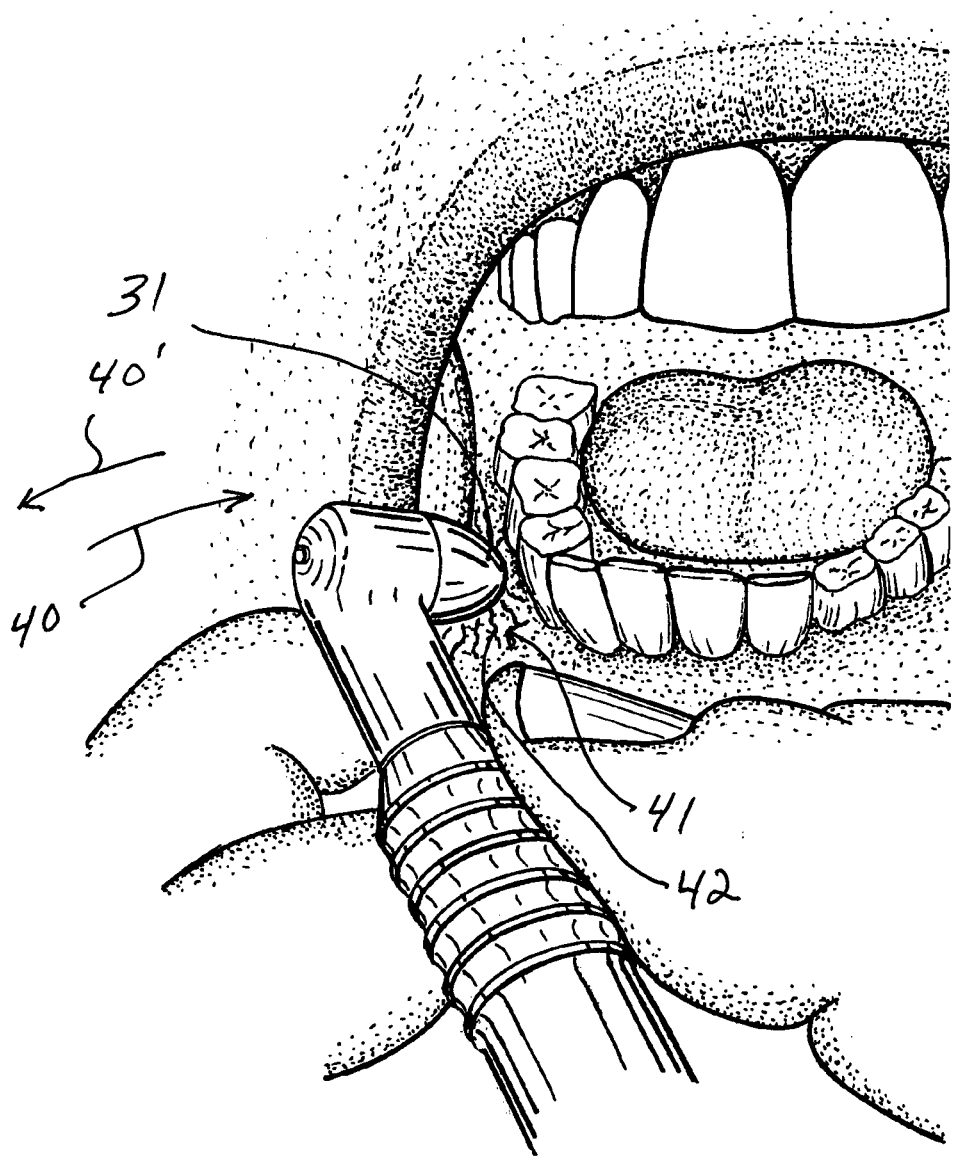
FIG. 6 is an isometric view of the vibrating tip of the invention of FIG. 1 as applied intra-orally to a patient.

Referring to FIG. 6, the vibrating 42 application surface 31 is then applied to the target area 41 of the patient (the area where the injection or other procedure is to be made) for a predetermined period of time, for example, 15-30 seconds, although the application time could vary from 1-60+ seconds, depending upon the patient's perception of pain, the severity of the procedure, etc. After the period of time has lapsed, the application surface is removed 40' from the area.

The care giver then may carefully apply the injection via needle, or other procedure to the application area, while judging the patient's perception of pain. If it is determined the patient still feels pain at an unacceptable level during application of the needle, the procedure utilizing the vibrating application tip to the target area may be repeated, until adequate numbing of the intra-oral soft tissue and adjacent area is determined.

The present device is designed to be universally utilized with a variety of low speed dental hand pieces which accept dental prophy angles.

In the present, preferred embodiment, the motor driving the hand piece is an air motor, and has a variably adjustable RPM of 30 to 30,000 via a standard dental foot pedal, which alters the air pressure running through the low-speed dental hand piece, although the device of the present invention is believed to have an optimal operational range of about 500 to 6,000 RPM. Because the system relies upon pneumatic air, there is thus no necessity for batteries or electrical outlets in the immediate area.

The design of the present device allows it to be manufactured at very low cost, believed less than $1.00 (one dollar U.S.) per unit. The device could be disposable and packaged in sterilized fashion so that no autoclaving by the care giver is ever necessary; the item is simply discarded after use on a patient.

Exemplary off-the-shelf low speed dental hand pieces which would be compatible include, for example:
1) KAVO INTRAMATIC™ brand low speed system.
2) HENRY SCHEIN MAXIMA™ brand low speed hand piece system.
3) STAR DENTAL TITAN™ brand low speed hand piece system.
4 MIDWEST™ brand low-speed hand piece systems.
5) Micro Motors, Inc. PHP™ brand series prophy hand pieces.

All of the above hand piece systems are operated by air driven motors and operate within an RPM range of 0-30,000. While virtually all dentists use air driven motors for their low-speed hand pieces, electric motors are starting to emerge in the marketplace, and would not be incompatible with the present system.

A summary of the method of the present invention, could comprise, for example, the steps of:

The method of preparing an intra-oral target area on a patent for treatment, comprising the steps of:

a) providing a device having:
 a first drive shaft having first and second ends said second end formed to rotate an off-center weight;
 a cover enveloping said off-center weight, at least part of said cover comprising an application surface;

b) applying said first end of said first drive shaft to a chuck associated with a hand piece;

c) applying said application surface to an intra-oral target area on a patient;

d) initiating a motor to rotate said chuck and first drive shaft, rotating said off center-weight to vibrate said application surface, so as to provide a vibrating application surface, e) utilizing said vibrating application surface to vibrate said target area on said patient for a pre-determined period of time, providing a treated target area;

f) disengaging said motor, ceasing rotation of said off-center weight, ceasing vibration of said application surface;

g) removing said application surface from said target area; and h) treating the patient at said treated target area.

A listing of the elements of the invention cited above follows:

| Element | Description |
| --- | --- |
| 1 | device |
| 2 | outer body casing |
| 3 | longitudinal portions |
| 4,' | first end, second end |
| 5 | lateral portion |
| 6,' | first, second ends |
| 7 | first, longitudinal drive shaft |
| 8,' | first, second ends |
| 9 | shank |
| 10 | emanating |
| 11 | 90 degree shaft gear |
| 12 | notch in base to engage hand piece |
| 13,' | support points for longitudinal drive shaft |
| 14 | second, lateral drive shaft |
| 15 | first, second ends |
| 16 | medial portion |
| 17 | hand piece |
| 18 | chuck |
| 19 | gear nub at fist end of lateral shaft |
| 20 | aperture in cover for first end of lateral shaft |
| 21 | 90 degree shaft gear engaging lateral drive shaft gear |
| 22 | off-center weight |
| 23 | collar engaging casing |
| 24 | nub |
| 25 | engage |
| 26 | notch |
| 30 | shell/cover portion |
| 31 | application surface |
| 32 | cavity |
| 33 | vibration |
| 34 | rotation |
| 40,' | applied, removed |
| 41 | target area |
| 42 | vibrating |

The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

I claim:

1. A device to facilitate intra-oral treatment of a patent's tissue, comprising:

an outer body casing having a longitudinal section having first and second ends, and a lateral section having first and second ends, said second end of said lateral section engaging said second end of said longitudinal section, said outer body casing having an inner wall forming a cavity therein;

a first drive shaft having first and second ends, said first drive shaft situated primarily within said longitudinal section of said outer body casing, said first end of said first drive shaft emanating from said first end of said longitudinal section of said outer body casing;

a second drive shaft having first and second ends, said second drive shaft situated within said lateral section of said outer body casing, said second end of said second drive shaft engaging said second end of said first drive shaft via first and second drive gears, respectively, said first end of said second drive shaft rotatably supporting an off-center weight;

said first end of said lateral section of said outer body casing forming a cover having an inner and outer surface, said inner surface of said cover enveloping said off-center weight, at least part of said outer surface of said cover comprising an application surface;

a collar emanating about said second drive shaft, said collar having an outer diameter configured to rotatingly engage said inner wall of said outer body casing, said collar formed to support and stabilize said second drive shaft;

a nub fixed to said inner surface of said cover, said nub formed to rotatingly engage said collar to said outer body casing such that vibratory force generated by the rotation of said off-center weight is conveyed via said collar, so as to provide said vibratory force to said application surface;

whereby upon applying said first end of said first drive shaft to a chuck associated with a hand piece, and engaging a motor associated with said chuck, said off-center weight is rotated to vibrate said inner surface of the outer body casing so as to conduct said vibration to said outer surface of said cover to said application surface, to form a vibrating surface, to provide intra-oral tissue numbing upon the application thereupon.

2. The device of claim 1, wherein said outer diameter of said collar has a groove thereabout formed to envelop said nub so as to engage said nub.

3. The device of claim 1, wherein said nub is formed to stabilize said collar while allowing the rotation of the collar, and to convey vibratory force from said collar to said inner surface of said cover, so as to provide vibratory force to said application surface.

* * * * *